United States Patent [19]

Hummelen et al.

[11] Patent Number: 4,778,767
[45] Date of Patent: Oct. 18, 1988

[54] SOLID PHASE IMMUNOASSAY USING IMMUNOREAGENTS IMMOBILIZED ON INERT SYNTHETIC RESIN SURFACES

[75] Inventors: Jan C. Hummelen; Theo Luider, both of Groningen; Hans Wynberg, Haren, all of Netherlands

[73] Assignee: Akzo N.V., Arnhem, Netherlands

[21] Appl. No.: 682,373

[22] Filed: Dec. 17, 1984

[51] Int. Cl.$^4$ .................................. G01N 33/545
[52] U.S. Cl. ................................ 436/531; 427/3;
435/7; 435/180; 436/534; 436/823; 436/824
[58] Field of Search .............. 436/531, 534, 823, 824;
435/7, 180; 427/3

[56] References Cited

U.S. PATENT DOCUMENTS

| | | | |
|---|---|---|---|
| 3,843,443 | 10/1974 | Fishman et al. | 435/181 |
| 4,017,597 | 4/1977 | Reynolds | 436/531 |
| 4,357,142 | 11/1982 | Schall, Jr. et al. | 435/7 |
| 4,360,358 | 11/1982 | Sharma | 436/534 |
| 4,444,879 | 4/1984 | Foster et al. | 436/513 |
| 4,705,847 | 11/1987 | Hummelen et al. | 530/350 |

OTHER PUBLICATIONS

Von Klitzing et al., Chemical Abstracts, vol. 99 (Sept. 1983) #101950j.
Boffa et al., Chemical Abstracts, vol. 86 (Jun. 1977) #195181r.
Von Kutzing et al., Chemical Abstracts, vol. 99 (Nov. 1983) #154586b.

*Primary Examiner*—Christine M. Nucker
*Attorney, Agent, or Firm*—William M. Blackstone

[57] ABSTRACT

A solid phase immunoassay comprises the steps of
(a) immobilizing an immunoreagent on the surface of a carrier comprised of an inert synthetic resin selected from the group consisting of polyimides and polyfluorinated synthetic resins,
(b) contacting the immunoreagent with a complementary immunoreagent whereby an immunocomplex immobilized on said carrier is formed,
(c) quantitating the immobilized immunocomplex.

An element useful in conducting this solid phase immunoassay is prepared by a process of treating the surface of an article comprised of a synthetic polymer selected from the group consisting of polyimides and polyfluorinated synthetic resins to make it adsorptive of an immunoreagent which comprises the steps of
(a) thoroughly rinsing the surface with a water-miscible organic solvent,
(b) thoroughly rinsing the surface with water.

42 Claims, 2 Drawing Sheets

SOLID PHASE IMMUNOASSAY USING IMMUNOREAGENTS IMMOBILIZED ON INERT SYNTHETIC RESIN SURFACES

BACKGROUND OF THE INVENTION

1. Field of the Invention

This invention relates to solid phase immunoassays using immobilized immunoreagents and more particularly to elements for solid phase immunoassay comprising immunoreagents immobilized on carriers made of inert synthetic resins. The invention also relates to methods of preparing synthetic resin surfaces for use as carriers for immunoreagents.

2. Description of the Prior Art

Immunoassay using immobilized immunoreagents is an analytical method widely used in biochemical analysis. In the conventional procedure an immunoreagent, e.g., an antigen or antibody, is first immobilized on the surface of an analytical element, e.g., a test tube, a rod or stick, beads of glass or plastic, or the like. The immobilized immunoreagent is then contacted with an analyte solution containing a complementary immunoreagent, whereby an immobilized immunocomplex is formed. The immobilized immunocomplex can then be easily separated from the unreacted analyte solution, e.g., by simply removing the analyte solution by aspiration, decantation, or the like, preferably with repeated washing of the immobilized immunocomplex. The separated immobilized immunocomplex may then be subjected to further processing to quantitate the amount of immunocomplex. For example, in a radioimmunoassay, the amount of adsorbed complex may be determined by counting radioactive disintegrations; in an enzyme-linked immunosorbent assay (ELISA) the adsorbed complex which has an enzyme coupled thereto, is contacted with a substrate for the enzyme to produce a detectable product; in an immunofluorescent assay, the fluorescent intensity of a fluorescent substance linked to the immunocomplex may be measured, or the like.

Among the many different materials which have been used as carriers for an immunoreagent are glass, metal, and various plastics such as polystyrene, polyvinyl chloride, silicone resins, polyethylene and the like. In some cases the immunoreagent has been immobilized by covalent bonding to the carrier, while in other cases adsorption of the immunoreagent has proved adequate. Synthetic resin carriers have been widely used because of their economy and convenience and ease of handling, but problems remain in immobilizing enough immunoreagent on their surfaces for maximum sensitivity of the immunoassay, especially when the reagent is merely adsorbed onto the surface. Furthermore, the synthetic resin carriers used previously are inadequate for some of the newer immunoassay techniques such as thermochemiluminescent immunoassay, which requires that the carrier with immobilized immunocomplex be heated to relatively high temperatures, i.e., 200° C. to 300° C. The conventional plastic carriers cannot be used under these conditions because they soften or even melt at such temperatures.

On the other hand, certain plastics are known which can be used at temperatures of 200° to 300° C. without melting or deformation, for example, polyimide synthetic resins, and polytetrafluoroethylene (PTFE) and related fluorinated olefin polymers. However, these resins are very inert and non-adhesive, and it has been thought that satisfactory adsorption of immunoreagents to such surfaces was not possible.

Prior workers in this field do not appear to have attempted to use a polyimide as a carrier for an immunoreagent in a solid phase immunoassay.

Some attempts have been made to use PTFE as a carrier for solid phase immunoassay, but the procedures have been unsuccessful or have had serious drawbacks.

Shekarchi, et al., J. Clin. Microbiology 16(6), 1012–1018 (December, 1982) disclose an immunoassay procedure wherein an immunoreagent is immobilized on a small stick, i.e., "microstick", for easy manipulation of the reagent and the immunocomplex. While a number of materials were investigated for use in such microsticks, including stainless steel, nylon, polycarbonate, polystyrene and PTFE, it was found that the PTFE, cleaned by the conventional procedure of rinsing with 6N HCl, adsorbed very little of the immunoreagent as compared with the other materials and could not be used as a base for the immunoreagent until it had been coated with polycarbonate or nitrocellulose.

German Offenlegungsschrift No. 32 00 822, published July 21, 1983, discloses a method for activating the surface of PTFE articles, in order to bond immunoreagents covalently, by contacting the PTFE surface with an ammoniacal solution of sodium, followed by treatment with carbodiimide. The process was apparently attempted because it was found that adsorption of the immunoreagent on PTFE was unsatisfactory. This process is complex and uses reagents which are difficult to handle and even dangerous. Furthermore, there is some question whether the procedure of this German application actually can immobilize a useful amount of immunoreagent on PTFE.

Hence, a need has continued to exist for improved immunoassay procedures using immunoreagents immobilized on inert carriers such as polyimides and fluorinated polymers and for a practical method of immobilizing immunoreagents on the surfaces of such synthetic resins.

SUMMARY OF THE INVENTION

It has now been found that a solid phase immunoassay element comprising an immunoreagent adsorbed onto the surface of a heat resistant synthetic resin such as a polyimide or PTFE can be prepared by adsorbing the immunoreagent onto the surface by simply incubating the surface in an aqueous solution of the immunoreagent, provided that the surface of the synthetic resin has first been cleaned by thorough rinsing with a water-miscible organic solvent followed by thorough rinsing with water.

The invention further comprises a solid phase immunoassay procedure using an immunoreagent immobilized on a carrier made of a polyimide or a polyfluorinated synthetic resin.

The invention further comprises a process for treating the surface of an article comprised of a synthetic polymer selected from the group consisting of polyimides and polyfluorinated synthetic resin polymers to make it receptive to adsorption of an immunoreagent this process comprising the steps of (a) thoroughly rinsing the surface with a water-miscible organic solvent, and (b) thoroughly rinsing the surface with water.

An immunoreagent may then be adsorbed onto the surface of the cleaned synthetic resin by contacting the surface with an aqueous solution of the immunoreagent.

Thus, it is an object of the invention to provide a method of solid phase immunoassay using an immunoreagent immobilized on the surface of an inert synthetic resin.

A further object is to provide an immobilized immunoreagent.

A further object is to provide an immunoreagent immobilized on a synthetic resin surface, where the synthetic resin is a polyimide or a polyfluorinated synthetic resin.

A further object is to provide a method for treating an inert synthetic resin surface to make it adsorptive to immunoreagents.

A further object is to provide a method of preparing an immobilized immunological reagent.

A further object is to provide a method of immobilizing an immunological reagent on a polyimide synthetic resin surface.

A further object is to provide a method of immobilizing an immunological reagent on a polyfluorinated polymer surface.

Further objects of the invention will become apparent from the description of the invention which follows.

DETAILED DESCRIPTION OF THE INVENTION AND PREFERRED EMBODIMENTS

Figure 1:
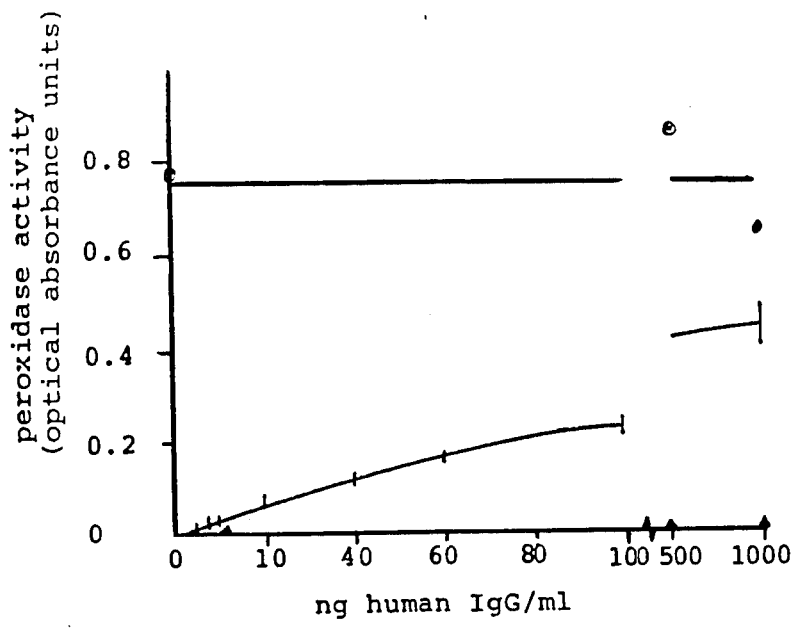
FIG. 1 illustrates the results of the solid phase enzyme-linked immunosorbent assay of Example 3 using a conventional polystyrene carrier.

The solid phase immunoassay of the invention using an immunoreagent immobilized on an inert resin surface of a polyimide or a polyfluorinated synthetic resin is capable of giving greater sensitivity than assays using immunoreagents immobilized on conventional carriers such as polystyrene and the like.

Solid phase immunoassay elements comprising an immunoreagent immobilized on a carrier surface of a polyimide or polyfluorinated synthetic resin are essential to the practice of the immunoassay of the invention. Such elements are useful in the practice of conventional immunoassays, but are especially useful for thermochemiluminescence immunoassays which require that the carrier with an immobilized immunocomplex be heated to relatively high temperatures, e.g., 200° C. to 300° C.

The solid phase immunoassay elements of this invention use carriers comprised of a polyimide or a polyfluorinated synthetic resin. The polyimide resins are inert heat-resistant synthetic resins which are characterized by the presence of the phthalimide structure in the backbone. A preferred polyimide is a condensation polymer of pyromellitic acid and bis(4-aminophenyl)oxide, sold by E. I. du Pont de Nemours & Co. under the name Kapton ®. The process may also employ polyfluorinated synthetic resins having surfaces of low surface energy which have hitherto been thought to be too non-adhesive for adsorption of immunoreagents. Such polymers include polymers of perfluorinated carbonates, polymers of perfluorinated epoxy compounds and especially addition polymers of ethylenically unsaturated hydrocarbons such as polytetrafluoroethylene, poly(chlorotrifluoroethylene) and the like. These materials are manufactured by a number of suppliers, e.g., by the Du Pont Co., under the name Teflon ®.

The water-miscible organic solvent used in the preparation of the immunoassay elements of the invention may be any solvent which can produce the requisite cleanliness of the surface of the synthetic resin, and is sufficiently miscible with water to be completely removed by subsequent thorough rinsing with water. Such solvents include lower aliphatic alcohols, e.g., $C_1$–$C_4$ aliphatic alcohols such as methanol, ethanol, n-propanol, isopropyl alcohol, n-butanol, isobutanol, sec.-butyl alcohol and tert.-butyl alcohol; lower aliphatic ketones, e.g., acetone, methyl ethyl ketone, and the like, dioxan, dimethylformamide, dimethyl sulfoxide, acetonitrile, lower ($C_1$–$C_4$) glycols such as ethylene glycol and propylene glycol, and lower aliphatic ethers having a total of about 3 to 6 carbon atoms, e.g., 2-methoxyethanol, 2-ethoxyethanol and the like. Mixtures of solvents may also be used. Preferred solvents are lower aliphatic alcohols, and a most preferred solvent is ethanol.

The solvent rinsing step is preferably conducted by contacting the surface of the synthetic resin with clean solvent for a period of time required to thoroughly clean the surface. The extract experimental conditions may vary with the solvent chosen, but the evaluation of the results in order to choose the proper condition may be simply carried out by using the surface in a standard immunoassay. A surface which has been inadequately cleaned will poorly adsorb the immunoreagent and manifest this poor adsorption by a low sensitivity in the immunoassay. It is preferable to have the solvent which contacts the synthetic resin surface as free as possible of contaminants. This can be accomplished by continuously supplying fresh solvent to the surface, e.g., in a flowing system, or by frequent changes of solvent when the cleaning is conducted by a batch process. The solvent will ordinarily be used in an anhydrous state for maximum solvent power for organic contaminants on the resin surface. However, the invention is also intended to include the use of solvents containing small amounts of water which do not seriously interfere with the solvent properties of the solvents toward organic surface contaminants.

It is preferred to conduct the solvent rinsing step by contacting the surface with the solvent at its boiling temperature. Accordingly water-miscible solvents having boiling points between about 40° C. and about 200° C. are preferred. The solvent rinsing step is therefore conveniently carried out by placing the articles to be coated, e.g., disks of the polymer to be used in immunosorbent assays, in a flask containing the solvent and heating to reflux temperature. The time of the solvent rinsing step will also vary depending on the solvent and its temperature. A relatively short contact time, e.g., one-half hour, may produce a surface which will adsorb some immunoreagent. However, it is preferable to keep the surface in contact with the solvent for a relatively long period of time, e.g., one or two days, in order to assure maximum cleaning and maximum adsorption of immunoreagent, which assures the highest sensitivity of the immunoassay. It is also preferable to change the solvent several times in the course of the rinsing step to insure maximum cleanliness of the solvent in the final portion of the rinsing step.

A preferred procedure is to contact the surface of the synthetic resin carrier with ethanol at refluxing temperature for a period of one to two days with frequency changes of solvent.

After the completion of the solvent cleaning step, the solvent-rinsed surface is then thoroughly rinsed with pure water, e.g., distilled or deionized water, to remove all traces of the solvent. Again, the preferable procedure is to immerse the articles in boiling water in a refluxing apparatus, for several hours, with several changes of water. The presence of residual solvent on the surface of the synthetic resin interferes with the adsorption of the immunoreagent and hence insufficient water rinsing is readily detected by the practitioner by simple use of a standard immunoassay. Evidently, the necessary length of the water rinsing step and the number of changes of fresh water can be easily determined by the practioner using this criterion.

If desired the carriers may be dried after the water rinsing step. The drying is preferably conducted by draining the water from the carriers and allowing the residual water to evaporate. It is preferable to assure complete dryness, especially when the carriers are to be used for a thermochemiluminescent assay, by drying in an oven at an elevated temperature, e.g., 200° C. to 300° C., for an extended period of time. Preferred drying conditions are 300° C. overnight.

The articles prepared by the cleaning process, either immediately after the rinsing step, without drying the surface, or after the surface has been dried, may then be coated with an immunoreagent by a relatively conventional adsorption step wherein the articles are contacted with an aqueous solution of the immunoreagent in a suitable buffer for a period of time to allow physical adsorption to occur to a sufficient extent. The basic process for this adsorption step is closed by Catt, U.S. Pat. No. 3,646,346. For example, the article may be contacted with an aqueous solution of an antibody at a concentration of 0.1 mg/ml in 0.1M tris(hydroxymethyl)aminomethane (Tris) at a pH of about 7.6 at 4° C. for an extended period of time, e.g. 2 or more days. The coated articles are then thoroughly washed with distilled water and are ready for use in immunoassay procedures.

Any immunoreagent conventionally used in immunoassay can be adsorbed to the surface of the inert synthetic resin carrier used in this invention. Ordinarily, the immunoreagent will be an antibody or an antigen and generally the immunoreagent will be a proteinaceous material.

While the preferred conditions are given above, effective ranges are rather broad, and it will be understood by those skilled in the art that the conditions may be varied, provided that the essential steps are performed. The success of the treatment under a given set of conditions is easily evaluated by simply measuring the amount of immunoreagent absorbed, e.g., by use in a conventional standard immunoassay.

The invention will be illustrated by the following examples which are not intended to be limiting. In the examples all parts and percentages are by weight.

EXAMPLE 1

This example illustrates the surface treatment process of process of this invention and immobilization of immunoreagent.

About 150 disks of a polyimide synthetic resin (Kapton 500H ®, manufactured by the du Pont company) having a diameter of 9 mm and a thickness of 125 micrometers were placed in a flask equipped with a reflux condenser, covered with ethanol, and rinsed with ethanol at reflux temperature for a period of one day with several changes of the ethanol solvent. The disks were then rinsed with distilled water at reflux temperature for several hours with several changes of distilled water. The disks were then removed from the flask and dried in an oven at a temperature of 300° C. overnight.

The dried disks were then placed in 40 ml of a solution of 0.1 mg/ml of antibody in 0.1M Tris buffer (pH 7.6) and 0.02% $NaN_3$, at a temperature of 4° C. The disks were gently shaken during the coating procedure which was continued for a period of 2 days. The coated disks were then washed in distilled water and could be preincubated, if desired, to prepare them for use in immunoassay by incubating them in an aqueous solution of 4% bovine serum albumin (BSA) in a 10 mM Tris buffer (pH 8.0), 0.15M NaCl, 0.05% polyoxyethylene sorbitan surfactant (Tween 20 ®) (Buffer A) for at least one hour.

EXAMPLE 2

The procedure of Example 1 was used to prepare and coat about 150 disks of polytetrafluoroethylene having a diameter of 9 mm and a thickness of 500 micrometers.

EXAMPLE 3

This example illustrates a comparison of ELISA conducted with the immunological reagent adsorbed by conventional procedures on a polystyrene microtiter plate and on carriers coated according to this invention.

Disks of polyimide or of polytetrafluorethylene were coated by the procedure of Example 1 with goat antihuman Immunoglobulin G (IgG) (7S) (Nordic), human IgG (Sigma) and BSA (Sigma). Polystyrene microtiter plates (Costar, Holland) were coated for one week with the same antibodies and with BSA by contacting them for a period of one week with a solution of 0.1 mg protein per ml, 0.1M carbonate buffer, pH 9.6, at a temperature of 4° C. Each well of the plates contained 0.1 ml of the solution. After the different carrier polymers were coated with the different immunoreagents, the solid phase immunoassay procedures were identical.

The coated carriers were preincubated for one hour with 0.2 ml of Buffer A. After washing with distilled water, the disks were incubated with 0.2 ml human IgG standards (0; 1; 2.5; 5; 7.5; 10; 20; 40; 60; 100; 500; 1000 ng human IgG per ml of Buffer A) for one hour at 37° C. while shaking in a waterbath. Subsequently, the disks were again washed with distilled water by decantation and incubated with 0.2 ml of an aqueous solution containing 1 microgram of peroxidase labeled goat-antihuman conjugate (Nordic) per milliliter of Buffer A at 37° C. in a waterbath with shaking. After removal of unbound conjugate, peroxidase activity on the disks was measured by means of the conversion of ortho-phenylenediamine to a colored product. Carriers coated with immunoreagent were incubated in the dark with 0.2 ml of M-phosphate buffer, pH 5.0, 0.0045% $H_2O_2$, $2 \cdot 10^{-3}$M ortho-phenylenediamine HCl (UCB) for one hour. Color development was stopped by adding of 0.5 ml of 1N $H_2SO_4$. The optical density of the color was measured at 495 nm with a Zeiss spectrophotometer.

Figure 2:
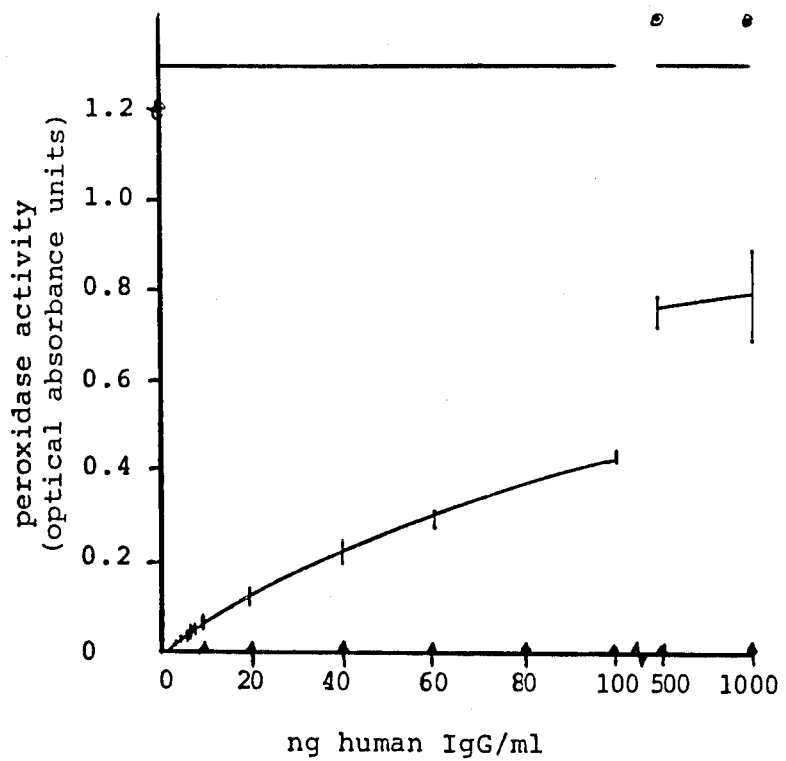
FIG. 2 illustrates the results of the solid phase enzyme-linked immunosorbent assay of Example 3 using a polyimide resin carrier.

FIG. 1 shows the results of an immunoassay on a polystyrene carrier. FIG. 2 shows the results of the same immunoassay using the polyimide (Kapton 500H ®) disks coated by the process of this invention.

Figure 3:
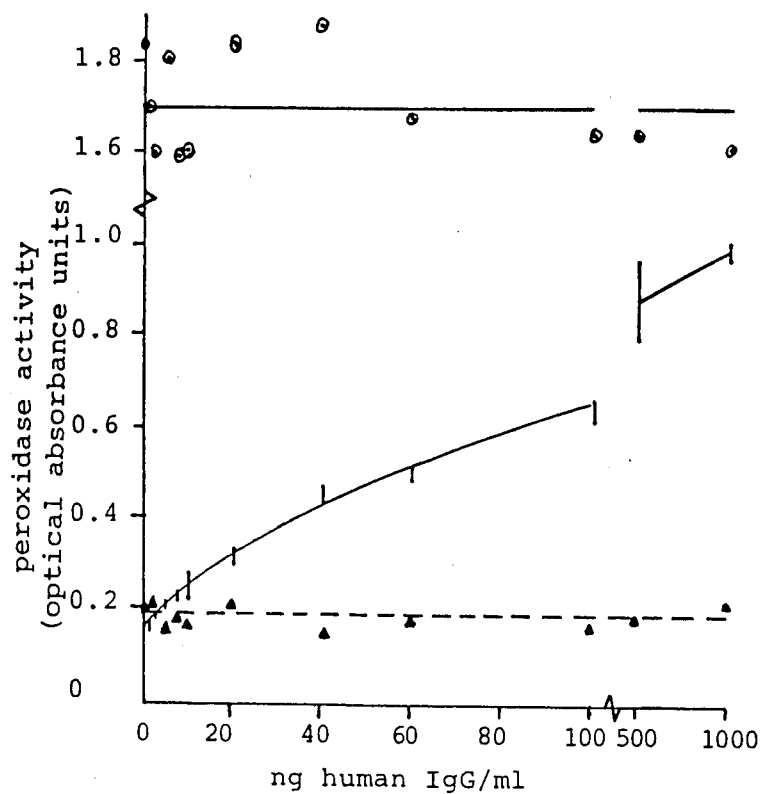
FIG. 3 illustrates the results of the solid phase enzyme-linked immunosorbent assay of Example 3 using a PTFE carrier.

FIG. 3 shows the results of the same immunoassay performed using PTFE disks coated by the process of this invention.

In the figures the symbols I indicate the values measured for the series of human IgG standards. Each data bar represents a triplicate measurement. The vertical length of the bar represents the range of the repeated determinations. Note that at a concentration below 20 ng/ml the measurements are so reproducible that the data bar has hardly any vertical length. The triangles indicate the measured values for the negative control (BSA) and the circles represent the measured values for the positive control (disks coated with pure antigen, human IgG).

FIGS. 2 and 3 show that the peroxidase activity of the adsorbed immunocomplex is substantially greater for the polyimide and PTFE carriers prepared according to this invention than for the conventional polystyrene carrier. Accordingly, is evident from the results of the experiment that the inert synthetic resin surfaces prepared and coated with immunoreagent by the process of this invention yield results superior to the conventional immunoassay using polystyrene microtiter plates.

EXAMPLE 4

This example illustrates the results of comparative immunoassays using polyimide carriers prepared by cleaning processes different from that of this invention.

A. Acidic cleaning treatment.

Kapton disks were contacted with 98% sulfuric acid for one minute at room temperature, washed with distilled water, and immediately (without drying) incubated with either human serum albumin (antigen) or human IgG (non-antigen). The incubated disks were then contacted with an aqueous solution of peroxidase-labeled rabbit-anti-human serum albumin (antibody). It was found that the amount of antibody bound to the carrier was the same for both the antigen-coated carrier and the carrier coated with non-antigen protein. Accordingly the antibody binding of the polyimide carrier prepared by an acid cleaning treatment is completely non-specific, and such a carrier is useless for solid phase immunoassay.

B. Basic cleaning treatment

Polyimide disks were treated with 5% KOH in distilled water for 5 minutes at room temperature, then washed a few times with distilled water. Analytical disks were then incubated with a series of human IgG standards of various concentrations according to the procedure of Example 3, while control disks were coated by incubation with a solution of bovine serum albumin (BSA). The immunoasay was conducted by the procedure of Example 3. It was found that the blank value of bound peroxidase activity (i.e., for the disks coated with BSA) was very high, about 0.80 to about 1.0 optical absorbance units. While the measured values of bound peroxidase activity for the disks coated with human IgG were measurably greater than the blank value, it is evident that such a high blank value produces an assay having inferior sensitivity and accuracy.

EXAMPLE 5

This example illustrates the specific nature of the pretreatment process of this invention Glass disks about 1.0 cm in diameter were treated by the process of Example 1 and used in an immunoassay as described in Example 3. It was found that the blank value (BSA coated disks) was rather high, about 0.25 optical absorbance units, while the measured value for an analyte concentration of 100 ng/ml (human IgG) was only about 0.40, i.e., only about 0.15 optical absorbance units greater than the blank value. The same process applied to glass beads about 5–7 mm in diameter gave even poorer results; the beads appeared to have no specific binding power after being subjected to the conventional adsorption process to coat them with an immunoreagent. Such results indicate that this process is not suitable for use with glass carriers. Accordingly, it is evident that the process of the invention is not a general cleaning process, but rather a cleaning process specially adapted to cleaning and preparing carriers of the claimed synthetic resins.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A solid phase immunoassay comprising the steps of
   (a) immobilizing an immunoreagent on the surface of a carrier comprised of an inert synthetic resin selected from the group consisting of polyimides,
   (b) contacting said immunoreagent with a complementary immunoreagent whereby an immunocomplex immobilized on said carrier is formed,
   (c) quantitating said immobilized immunocomplex.

2. The immunoassay of claim 1 wherein said polyimide is a polymer of pyromellitic acid and bis(4-aminophenyl)oxide.

3. The immunoassay of claim 1 wherein said immunoreagent is a protein.

4. The immunoassay of claim 1 wherein said immunoreagent is an antibody.

5. The immunoassay of claim 1 wherein said immunoreagent is an antigen.

6. An element for use in a solid phase immunoassay comprising an immunoreagent immobilized on the surface of a carrier comprised of an inert synthetic resin selected from the group consisting of polyimides.

7. The element of claim 6 wherein said polyimide is a polymer of pyromellitic acid and bis(4-aminophenyl)oxide.

8. The element of claim 6 wherein said immunoreagent is a protein.

9. The element of claim 6 wherein said immunoreagent is an antibody.

10. The element of claim 6 wherein said immunoreagent is an antigen.

11. The immunoassay of claim 1 wherein the surface of the carrier is treated to make it receptive to adsorption of an immunoreagent prior to immobilizing an immunoreagent thereon by the process comprising the steps of
    (a) thoroughly rinsing the surface with a water-miscible organic solvent, and
    (b) thoroughly rinsing the surface with water.

12. The immunoassay of claim 11 wherein said solvent is a $C_1$–$C_4$ aliphatic alcohol.

13. The immunoassay of claim 12 wherein said alcohol is ethanol.

14. The immunoassay of claim 11 wherein said solvent rinsing step is carried out at a temperature equal to the boiling point of the solvent.

15. The immunoassay of claim 11 wherein said solvent rinsing step is carried out for a period of from about one-half hour to about four days.

16. The immunoassay of claim 15 wherein said solvent rinsing step is carried out for at least one day.

17. The immunoassay of claim 11 wherein said water rinsing step is carried out at a temperature equal to the boiling point of water.

18. The immunoassay of claim 11 wherein the surface of the carrier is dried after the water rinsing step.

19. The immunoassay of claim 18 wherein said drying step is carried out at a temperature greater than 200° C.

20. The immunoassay of claim 19 wherein said drying step is carried out at a temperature of about 300° C.

21. The immunoassay of claim 11 wherein the treated surface is contacted with an aqueous solution containing an immunoreagent.

22. A solid phase thermochemiluminescent immunoassay comprising the steps of
   (a) thoroughly rinsing the surface of a carrier comprised of an inert synthetic resin selected from the group consisting of polyfluorinated synthetic resins with a water-miscible organic solvent,
   (b) thoroughly rinsing the surface of the carrier with water,
   (c) contacting the surface of the carrier with an aqueous solution of a first immunoreagent for a sufficient time to immobilize at least a portion of the first immunoreagent on said surface,
   (d) contacting said immobilized first immunoreagent with a complementary immunoreagent whereby an immunocomplex immobilized on said carrier is formed,
   (e) contacting the surface of the carrier having the immobilized immunocomplex thereon with an immunoreagent that is immunoreactive with either the complementary immunoreagent or the first immunoreagent and has a thermochemiluminescent label to form a detectable labelled immunocomplex immobilized on said carrier,
   (f) heating said carrier to a temperature at which the thermochemiluminescent label becomes luminescent, and
   (g) detecting said immobilized thermochemiluminescent immunocomplex.

23. The immunoassay of claim 22 wherein said polyfluorinated synthetic resin is a polymer of a polyfluorinated ethylenically unsaturated hydrocarbon.

24. The immunoassay of claim 23 wherein said polyfluorinated synthetic resin is polytetrafluoroethylene.

25. The immunoassay of claim 22 wherein said first immunoreagent is a protein.

26. The immunoassay of claim 22 wherein said first immunoreagent is an antibody.

27. The immunoassay of claim 22 wherein said first immunoreagent is an antigen.

28. The immunoassay of claim 22 wherein said solvent is a $C_1$–$C_4$ aliphatic alcohol.

29. The immunoassay of claim 28 wherein said alcohol is ethanol.

30. The immunoassay of claim 22 wherein solvent rinsing is carried out at a temperature equal to the boiling point of the solvent.

31. The immunoassay of claim 22 wherein solvent rinsing is carried out for a period of from about one-half hour to about four days.

32. The immunoassay of claim 31 wherein solvent rinsing is carried out for at least one day.

33. The immunoassay of claim 22 wherein water rinsing is carried out at a temperature equal to the boiling point of water.

34. The immunoassay of claim 22 wherein the surface of the carrier is dried after water rinsing.

35. The immunoassay of claim 34 wherein said drying step is carried at a temperature greater than 200° C.

36. The immunoassay of claim 35 wherein said drying step is carried out at a temperature of about 300° C.

37. An element for use in the solid phase thermochemiluminescent immunoassay of claim 22, comprising an immunoreagent immobilized on the surface of a carrier comprised of an inert synthetic resin selected from the group consisting of polyfluorinated synthetic resins, wherein the surface of the carrier has been prepared by thorough washing with a water-miscible organic solvent followed by thorough washing with water before immobilizing the immunoreagent thereon.

38. The element of claim 37 wherein said polyfluorinated synthetic resin is a polymer of a polyfluorinated ethylenically unsaturated hydrocarbon.

39. The element of claim 38 wherein said polyfluorinated synthetic resin is polytetrafluoroethylene.

40. The element of claim 37 wherein said immunoreagent is a protein.

41. The element of claim 37 wherein said immunoreagent is an antibody.

42. The element of claim 37 wherein said immunoreagent is an antigen.

* * * * *